(12) United States Patent
Tanaka et al.

(10) Patent No.: US 7,700,541 B2
(45) Date of Patent: *Apr. 20, 2010

(54) BIODEGRADABLE CATIONIC POLYMERS (75) Inventors: Yasunobu Tanaka, San Diego, CA (US); Gang Zhao, Vista, CA (US); Lei Yu, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 118 days.

This patent is subject to a terminal disclaimer.

(21) Appl. No.: 11/695,365

(22) Filed: Apr. 2, 2007

(65) Prior Publication Data

US 2007/0243157 A1 Oct. 18, 2007

Related U.S. Application Data (60) Provisional application No. 60/789,842, filed on Apr. 6, 2006.

(51) Int. Cl.
*A01N 61/10* (2006.01)
*A01N 43/04* (2006.01)
*C08F 10/00* (2006.01)

(52) U.S. Cl. ............... 514/1; 514/44; 525/100; 536/23.1; 536/24.5; 424/1.45; 977/704

(58) Field of Classification Search ............ None
See application file for complete search history.

(56) References Cited

U.S. PATENT DOCUMENTS

| | | | |
|---|---|---|---|
| 5,374,681 A | 12/1994 | Kroner et al. | |
| 5,811,510 A | 9/1998 | Papisov | |
| 5,863,990 A | 1/1999 | Papisov | |
| 5,958,398 A | 9/1999 | Papisov | |
| 6,025,337 A | 2/2000 | Truong et al. | |
| 6,159,591 A | 12/2000 | Beihoffer et al. | |
| 6,231,960 B1 | 5/2001 | Dyer et al. | |
| 6,319,516 B1 | 11/2001 | Huang et al. | |
| 6,569,528 B2 | 5/2003 | Nam et al. | |
| 6,586,524 B2 | 7/2003 | Sagara | |
| 6,652,886 B2 | 11/2003 | Ahn et al. | |
| 6,696,038 B1 | 2/2004 | Mahato et al. | |
| 6,878,374 B2 | 4/2005 | Yu et al. | |
| 7,125,709 B2 | 10/2006 | Tanaka et al. | |
| 7,358,223 B2 * | 4/2008 | Zhao et al. ............ | 514/1 |
| 2002/0006664 A1 | 1/2002 | Sabatini et al. | |
| 2002/0052443 A1 | 5/2002 | Greenwald et al. | |
| 2002/0082362 A1 | 6/2002 | Brocchini et al. | |
| 2002/0131951 A1 | 9/2002 | Langer et al. | |
| 2003/0120355 A1 | 6/2003 | Hafeli et al. | |
| 2003/0186916 A1 | 10/2003 | Yu et al. | |
| 2003/0215395 A1 | 11/2003 | Yu et al. | |
| 2004/0048260 A1 | 3/2004 | Chang et al. | |
| 2004/0071654 A1 | 4/2004 | Anderson et al. | |
| 2004/0138154 A1 | 7/2004 | Yu et al. | |
| 2004/0166089 A1 | 8/2004 | Yu et al. | |
| 2005/0037401 A1 | 2/2005 | Cammack et al. | |
| 2005/0049387 A1 | 3/2005 | Van et al. | |
| 2005/0080033 A1 | 4/2005 | Van et al. | |
| 2005/0089503 A1 | 4/2005 | Li et al. | |
| 2006/0257320 A1 | 11/2006 | Van et al. | |
| 2006/0258751 A1 | 11/2006 | Zhao et al. | |
| 2006/0263328 A1 | 11/2006 | Van et al. | |
| 2007/0020761 A1 | 1/2007 | Yu et al. | |
| 2007/0072171 A1 | 3/2007 | Yu et al. | |
| 2007/0269891 A9 | 11/2007 | Tanaka et al. | |
| 2008/0207553 A1 | 8/2008 | Zhao et al. | |

FOREIGN PATENT DOCUMENTS

| | | |
|---|---|---|
| EP | 1 279 682 | 1/2003 |
| WO | WO 95/25809 | 9/1995 |
| WO | WO 97/45069 | 5/1997 |
| WO | WO 02/22174 | 3/2002 |
| WO | WO 2005/060934 | 7/2005 |
| WO | WO 2006/041617 | 4/2006 |
| WO | WO 2007/081429 | 7/2007 |
| WO | WO 2007/120479 | 10/2007 |

OTHER PUBLICATIONS

Akinc et al., "Parallel Synthesis and Biophysical Characterization of a Degradable Polymer Library for Gene Delivery," J. Am. Chem. Soc. 125, 5316-5323 (2003).

Barrera et al., Synthesis and RGD Peptide Modification of a New Biodegradable Copolymer: Poly(lactic acid-co-lysine), J. Am. Chem. Soc. 115, 11010-11011 (1993).

Boussif et al., "A versatile vector for gene and oligonucleotide transfer into cells in culture and in vivo: Polyethylenimine," Proc Natl Acad Sci USA. Aug. 1, 1995, 92(16) 7297-7301.

Cotten, et al., "High-efficiency receptor-mediated delivery of small and large (48 Kilobase gene constructs using the endosome-disruption activity of defective or chemically inactivated adenovirus particles," (Jul. 1992) Proc. Natl. Acad. Sci. USA vol. 89: pp. 6094-6098.

Eichman et al., "The use of PAMAM dendrimers in the efficient transfer of genetic material into cells," Pharm. Sci. Technol. Today Jul. 2000; 3(7):232-245.

Gosselin et al., "Efficient Gene Transfer Using Reversibly Cross-Linked Low Molecular Weight Polyethylenimine," Bioconjugate Chem. 2001. 12:989-994.

Gottschalk, et al., "Folate receptor mediated DNA delivery into tumor cells: potosomal disruption results in enhanced gene expression," (1994) Gene Ther 1:185-191.

Kwon et al., Pseudopoly(amino acids): A Study of the Syntheses and Characterization of Poly(*trans*-4-hydroxy-*N*-acly-L-proline esters), Macromolecules, 22, 3250-3255 (1989).

(Continued)

*Primary Examiner*—Richard Schnizer
(74) *Attorney, Agent, or Firm*—Knobbe, Martens, Olson & Bear LLP (57) ABSTRACT Polymers comprising a polyethylenimine having a molecular weight less than 600 Daltons, a biodegradable group, and a relatively hydrophobic group that are useful for the delivery of bioactive agents to cells.

23 Claims, 2 Drawing Sheets

OTHER PUBLICATIONS

Lim et al., A Self-Destroying Polycationic Polymer: Biodegradable Poly(4-hydroxy-L-proline ester), J. Am. Chem. Soc. 121, 5633-5639 (1999).

Lim et al., "Cationic Hyperbranched Poly(amino ester): A Novel Class of DNA Condensing Molecule with Cationic Surface, Biodegradable Three-Dimensional Structure, and Tertiary Amine Groups in the Interior," J. Am. Chem. Soc., 123, 2460-2461 (2001).

Lynn et al., "Accelerated Discovery of Synthetic Transfection Vectors: Parallel Sythesis and Screening of a Degradable Polymer Library," J. Am. Chem. Soc. 123, 8155-8156 (2001).

Marshall, E., "Gene Therapy Death Prompts Review of Adenovirus Vector," Science (1999) 286: 2244-2245.

Putnam et al., "Poly(4-hydroxy-L-proline ester): Low-Temperature Polycondensation and Plasmid DNA Complexation," Macromolecules, 32, 3658-3662 (1999).

Sharma et al., "Molecular Imaging of Gene Expression and Protein Function In Vivo With PET and SPECT," Journal of Magnetic Resonance Imaging 16:336-351 (2002).

Uherek, et al., "A Modular DNA Carrier Protein Based on the Structure of Diphtheria Toxin Mediates Target Cell-specific Gene Delivery," (1998) J Biol. Chem. vol. 273: 8835-8841.

Verma I.M and Somia N., "Gene therapy—promises, problems and prospects," Nature 389 (1997), pp. 239-242.

Wagner, et al. "Transferrin-polycation conjugates as carriers for DNA uptake into cells," (1990) Proc Natl Acad Sci USA vol. 87: 3410-3414.

Zhou et al., Preparation of Poly(L-serine ester): A Structural Analogue of Conventional Poly(L-serine ester), Macromolecules, 23, 3399-3406 (1990).

International Search Report and Written Opinion dated Mar. 22, 2006 for International Patent Application No. PCT/US2005/033274.

International Search Report and Written Opinion dated Jan. 10, 2007 for International Patent Application No. PCT/US2007/008106.

Notice of Allowance dated Nov. 28, 2007 for U.S. Appl. No. 11/216,986.

International Preliminary Report on Patentability dated Oct. 8, 2008 for International Patent Application No. PCT/US2007/008106.

International Preliminary Report on Patentability dated Apr. 11, 2007 for International Patent Application No. PCT/US2005/033274.

Office Action dated Mar. 5, 2009 for U.S. Appl. No. 12/014,446.

Bielinska et al., "Application of membrane-based dendrimer/DNA complexes for solid phase transfection in vitro and in vivo," Biomaterials (2000) 21(9):877-887.

Bledi et al., "Culturing neuronal cells on surface coated by a novel polyethyleneimine-based polymer," Brain Research Protocols (2000) 5(3):282-289.

Chang et al., "Surfection: a new platform for transfected cell arrays," Nucleic Acid Res. (2004) 32(3)e33: 1-6.

Clark et al. "Cationic lipid-mediated gene transfer: current concepts," Curr Opin Mol Ther (1999) 1(2):158-176 (Abstract only).

De Semir et al., "Non-viral vector-mediated uptake, distribution, and stability of chimeraplasts in human airway epithelial cells," J. Gene Med. (2002) 4(3):308-322.

Dwyer et al., "Attachment of PC12 cells to adhesion substratum induces the accumulation of glucose transporters (GLUTs) and stimulates glucose metabolism," Neurochem Res. (1998) 23(8):1107-1116.

Kircheis et al., "Tumor-targeted gene delivery of tumor necrosis factor-$\alpha$ induces necrosis and tumor regression without systemic toxicity," Cancer Gene Ther. (2002) 9(8):673-680.

Luo et al., "Enhancement of transfection by physical concentration of DNA at the cell surface," Nature Biotechnology (2000) 18(8):893-895.

Lynn et al., "Degradable Poly($\beta$-amino ester): Synthesis, Characterization, and Self-Assembly with Plasmid DNA," J. Am. Chem. Soc. (2000) 122:10761-10768.

Petersen et al., "Poly(ethylenimine-co-L-lactamide-co-succinamide): A Biodegradable Polyethlenimine Derivative with an Advantageous pH-Dependent Hydrolytic Degradation for Gene Delivery," Bioconjugate Chem. (2002) 13(4):812-821.

Pollard et al., "Polyethylenimine but not cationic lipids promotes transgene delivery to the nucleus in mammalian cells.," J. Biol. Chem. (1998) 273(13):7507-7511.

Segura et al., "Surface-tethered DNA complexes for enhanced gene delivery," Bioconjugate Chem. (2002) 13(3):621-629.

Vancha et al., "Use of polyethyleneimine polymer in cell culture as attachment factor and lipofection enhancer," BMC Biotechnol. (2004) 4(23):1-12.

Zheng et al., "Transfection of cells mediated by biodegradable polymer materials with surface-bound polyethyleneimine," Biotechnol Prog. (2000) 16(2): 254-257.

Ziauddin et al., "Microarrays of cells expressing defined cDNAs," Nature (2001) 411(6833):107-110.

International Search Report dated Oct. 31, 2003 for International Application PCT / US03/15003 filed May 13, 2005.

Office Action for U.S. Appl. No. 10/270,788 mailed Nov. 30, 2005.

\* cited by examiner

SEQUENCE LISTING

<160> NUMBER OF SEQ ID NOS: 2

<210> SEQ ID NO 1
<211> LENGTH: 7
<212> TYPE: PRT
<213> ORGANISM: Simian virus 40

<400> SEQUENCE: 1

Pro Lys Lys Lys Arg Lys Val
1               5

<210> SEQ ID NO 2
<211> LENGTH: 21
<212> TYPE: RNA
<213> ORGANISM: Artificial Sequence
<220> FEATURE:
<223> OTHER INFORMATION: Synthetically prepared ribonucleic acid
      sequence
<220> FEATURE:
<221> NAME/KEY: misc_feature
<222> LOCATION: 1, 2
<223> OTHER INFORMATION: n = A,U,C or G

<400> SEQUENCE: 2
nncgagaagc gcgaucacau g                                              21

BIODEGRADABLE CATIONIC POLYMERS

CROSS-REFERENCE TO RELATED APPLICATIONS

This application claims priority to U.S. Provisional Application No. 60/789,842, filed Apr. 6, 2006, which is hereby incorporated by reference in its entirety including all drawings. Additionally, this application is related to U.S. patent application Ser. No. 11/216,986, filed Aug. 31, 2005, now U.S. Pat. No. 7,358,223, which is hereby incorporated by reference in its entirety including all drawings.

SEQUENCE LISTING

The present application is being filed along with a Sequence Listing in electronic format. The Sequence Listing is provided as a file entitled NDTCO.056A.TXT, created Feb. 5, 2007, which is 1 Kb in size. The information in the electronic format of the Sequence Listing is incorporated herein by reference in its entirety.

BACKGROUND OF THE INVENTION

1. Field of the Invention

This invention relates to compositions and methods for delivering bioactive agents to cells. Specifically, this invention relates to cationic lipopolymers comprising a poly- or oligo-ethyleneimine (PEI), a biodegradable group, and a relatively hydrophobic group, and to methods of making and using such lipopolymers to deliver oligonucleotides such as siRNA and antisenses.

2. Description of the Related Art

A number of techniques are available for delivering bioactive agents such as plasmids DNA to cells, including the use of viral transfection systems and non-viral transfection systems. Viral systems typically have higher transfection efficiency than non-viral systems, but there have been questions regarding the safety of viral systems. See Verma I. M and Somia N., Nature 389 (1997), pp. 239-242; Marhsall E. Science 286 (2000), pp. 2244-2245. In addition, viral vector preparation tends to be a complicated and expensive process. Although non-viral transfection systems generally are less efficient than viral systems, they have received significant attention because they are generally believed to be safer and easier to prepare than viral systems.

A number of non-viral transfection systems involve the use of cationic polymers that are complexed to plasmids DNA. Examples of cationic polymers that have been used as gene carriers include poly(L-lysine) (PLL), polyethyleneimine (PEI), chitosan, PAMAM dendrimers, and poly(2-dimethylamino)ethyl methacrylate (pDMAEMA). Unfortunately, transfection efficiency is typically poor with PLL, and high molecular weight PLL has shown significant toxicity to cells. In some cases, PEI that range in molecular weight from 20,000 to 25,000 Daltons provides efficient gene transfer without the need for endosomolytic or targeting agents. See Boussif O., Lezoualc'h F., Zanta M. A., Mergny M. D., Scherman D., Demeneix B., Behr J. P., Proc Natl Acad Sci USA. Aug. 1, 1995, 92(16) 7297-301. However, PEI that range in molecular weight from 400 to 2,000 Daltons is not effective for plasmids DNA delivery. A range of polyamidoamine dendrimers have been studied as gene-delivery systems. See Eichman J. D., Bielinska A. U., Kukowska-Latallo J. F., Baker J. R. Jr., Pharm. Sci. Technol. Today 2000 July; 3(7): 232-245. Unfortunately, both PEI and dendrimers have been reported to be toxic to cells, thus limiting the potential for using PEI as a gene delivery tool in applications to human patients. In addition, the cost of polyamidoamine dendrimers having commercially practical gene transfection efficiencies is relatively high.

Gene, such as plasmids DNA, carriers made with degradable cationic polymers have been reported to transfer genes into mammalian cells with decreased cytotoxicity. See Lim Y. B., Kim S. M., Lee Y., Lee W. K., Yang T. G., Lee M. J., Suh H., Park J. S., J. Am. Chem. Soc., 123 (10), 2460-2461, 2001. Unfortunately, these degradable systems also exhibited lower plasmids DNA transfer efficiency compared to non-degradable polymers. To improve the transfection efficiency of low molecular weight PEI, Gosselin et al. reported that higher molecular weight PEI could be obtained by using disulfide-containing linkers with lower molecular weight PEI. See Gosselin, Micheal A., Guo, Menjin, and Lee, Robert J. Bioconjugate Chem. 2001. 12:232-245. PEI polymers made using dithiobis(succinimidylpropionate) (DSP) and dimethyl-3,3'-dithiobispropionimidate-2HCl (DTBP) showed comparable gene transfection efficiency and lower cytotoxicity. However, the disulfide-containing linkers are expensive, which makes large-scale preparation of this system difficult and undesirable. The polymers with disulfide-containing linkers are only degraded under reducing conditions, which limits polymer applications in other conditions.

Lynn, et al. have described a method of synthesizing biodegradable cationic polymers using diacrylates as linker molecules between cationic compounds. See Lynn, David A.; Anderson, Daniel G.; Putnam, David; and Langer, Robert. J. Am. Chem. Soc. 2001, 123, 8155-8156. However, synthesis of these polymers require days to complete and the amount of effective product, which can be used in gene delivery, is low. More than one hundred cationic polymers were produced according to the methods of Lynn et al., but only two of these polymers showed effective gene transfection efficiency. Cationic polymers such as PEI have not been shown to be effective for siRNA delivery. The biodegradable cationic polymer produced accordingly to the methods of Lynn et al., have not been used to deliver siRNA or oligonucleotides.

Thus, there remains a need for cationic polymers that may be used to safely and efficiently facilitate the delivery of siRNA and oligonucleotides to cells.

SUMMARY OF THE INVENTION

The inventors have discovered several polymer compositions that are capable of delivering oligonucleotides to cells. In certain embodiments, the polymer can be further complexed to other moieties such as a delivery enhancing agent and/or a diagnostic imaging compound. In addition, the inventors have discovered methods for delivering an oligonucleotide to the cell(s) using the polymer compositions.

One embodiment disclosed herein includes a polymer comprising a recurring unit selected from the group consisting of formula (I):

wherein PEI can be a polyethyleneimine recurring unit having a molecular weight less than 600 Daltons. R can be selected from the group consisting of electron pair, hydrogen, $C_2$-$C_{10}$ alkyl, $C_2$-$C_{10}$ heteroalkyl, $C_5$-$C_{30}$ aryl, and $C_2$-$C_{30}$ heteroaryl, L can be selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{10}$ aryl, $C_2$-$C_{50}$ heteroaryl, $C_2$-$C_{50}$ alkynyl, $C_2$-$C_{50}$ heteroalkynyl, $C_2$-$C_{50}$ carboxyalkenyl and $C_2$-$C_{50}$ carboxyheteroalkenyl and m is an integer that can be in the range of about 1 to about 30.

In one embodiment, the PEI can comprise at least one recurring unit selected from the group consisting of formula (IIa) and formula (IIb):

wherein x is an integer in the range of about 1 to about 12, y is an integer in the range of about 1 to about 6, and z is an integer in the range of about 1 to about 13.

The polymer, in some embodiments, can be biodegradable. Suitable mechanisms by which the polymer can degrade include, but are not limited to, hydrolysis, enzyme cleavage, reduction, photo-cleavage, and sonication.

In some embodiments, L can be selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_2$-$C_{50}$ alkynyl and $C_2$-$C_{50}$ heteroalkynyl. In other embodiments, L can be selected from the group consisting of $C_{12}$ to $C_{18}$ fatty acid, cholesterol and derivatives thereof.

The polymer can have a weight average molecular weight, in one embodiment, in the range of about 500 Daltons to about 1,000,000 Daltons. In another embodiment, the polymer can have a weight average molecular weight in the range of about 1,000 Daltons to about 200,000 Daltons.

In some embodiments, the polymer can be crosslinked.

Another embodiment disclosed herein includes the polymer which can further comprise an oligonucleotide that is complexed to the polymer. Examples of suitable oligonucleotides include, but are not limited to, RNA oligomers such as siRNA and DNA oligomers such as antisenses.

In addition to the oligonucleotide, the polymer can further comprise a delivery enhancing agent capable of entering a eukaryotic cell. If desired, the polymer can further comprise a diagnostic imaging compound that can be complexed to the polymer. The delivery enhancing agent can facilitate one or more of the following functions in the eukaryotic cell: receptor recognition, internalization, escape of the oligonucleotide from cell endosome, nucleus localization, oligonucleotide release and system stabilization. Exemplary oligonucleotides include but are not limited to siRNA and antisense. In other embodiments, the delivery enhancing agent can be coupled to the polymer.

One embodiment disclosed herein includes a method of transfecting a eukaryotic cell, comprising contacting the cell with the polymer to thereby deliver the oligonucleotide to the cell, wherein the polymer can further comprise an oligonucleotide.

Another embodiment disclosed herein include a method of treating a mammal comprising identifying a mammal in need of gene therapy and administering the polymer that is conjugated to an oligonucleotide to the mammal, wherein the oligonucleotide comprises an siRNA that is effective to lower or silence expression of the gene of interest.

In some embodiments, the polymer can further comprise a diagnostic imaging compound that is complexed to the polymer. One embodiment disclosed herein includes a method of delivering the diagnostic imaging compound to a mammal, comprising administering the polymer to a mammal, wherein the polymer is complexed to the diagnostic imaging compound.

One embodiment disclosed herein includes a polymer library comprising a plurality of the polymers, wherein at least one parameter selected from the group consisting of R, L, PEI and m is different for at least two of the polymers.

Another embodiment disclosed herein includes a medical diagnostic system comprising the polymer and a ligand that can recognize a specific receptor of a eukaryotic cell. If desired, the polymer can be coupled to the ligand.

In still another embodiment disclosed herein a pharmaceutical composition can comprise a sensitizer agent and the polymer. The sensitizer agent can be sensitive to visible radiation, ultraviolet radiation, or both. In one embodiment, the pharmaceutical composition can comprise a sensitizer agent and the polymer, wherein the polymer can have an affinity for an oligonucleotide.

In one embodiment, a diagnostic imaging composition can comprise an image contrast agent and the polymer. If desired, the diagnostic imaging composition can further comprise a targeting agent.

One embodiment disclosed herein includes a polymer comprising a recurring unit selected from the group consisting of formula (I):

wherein PEI is a polyethyleneimine recurring unit comprising at least one recurring unit of the formula (IIb):

wherein z is an integer in the range of about 1 to about 13. R can be selected from the group consisting of electron pair, hydrogen, $C_2$-$C_{10}$ alkyl, $C_2$-$C_{10}$ heteroalkyl, $C_5$-$C_{30}$ aryl, and $C_2$-$C_{30}$ heteroaryl. L can be selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl, $C_2$-$C_{50}$ heteroaryl, $C_2$-$C_{50}$ alkynyl, $C_2$-$C_{50}$ heteroalkynyl, $C_2$-$C_{50}$ carboxyalkenyl and $C_2$-$C_{50}$ carboxyheteroalkenyl; and m is an integer that can be in the range of about 1 to about 30.

In one embodiment, the PEI comprising at least one recurring unit of the formula (IIb) can have a molecular weight of less than 600 Daltons.

In some embodiments, the PEI further comprises a recurring unit of the formula IIa:

wherein x can be an integer in the range of about 1 to about 12 and y can be an integer in the range of about 1 to about 6.

In one embodiment, the polymer, wherein the PEI further comprises a recurring unit of formula (IIa), can have a molecular weight of less than 600 Daltons.

DETAILED DESCRIPTION OF THE PREFERRED EMBODIMENT

An embodiment provides cationic lipopolymers comprising a polyethylenimine, a biodegradable group, and a relatively hydrophobic "lipo" group. Preferred cationic lipopolymers comprise a recurring unit selected from the group consisting of formula (I):

In formula (I), PEI is polyethyleneimine, the ester linkages are biodegradable groups, and L represents a relatively hydrophobic "lipo" group. For example, in certain embodiments L is selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl; $C_2$-$C_{50}$ heteroaryl; $C_2$-$C_{50}$ alkynyl, $C_2$-$C_{50}$ heteroalkynyl, $C_2$-$C_{50}$ carboxyalkenyl and $C_2$-$C_{50}$ carboxyheteroalkenyl. In preferred embodiments, L is selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_2$-$C_{50}$ alkynyl and $C_2$-$C_{50}$ heteroalkynyl. In the more preferred embodiments, L is selected from the group consisting of $C_{12}$ to $C_{18}$ fatty acid, cholesterol, and derivatives thereof.

The R in formula (I) may represent an electron pair or a hydrogen atom. Those skilled in the art understand that when R represents an electron pair, the recurring unit of formula (I) is cationic at low pH. The R in formula (I) may also represent a relatively hydrophobic lipo group such as $C_2$-$C_{10}$ alkyl, $C_2$-$C_{10}$ heteroalkyl, $C_5$-$C_{30}$ aryl, or $C_2$-$C_{30}$ heteroaryl, in which case it will be understood that the nitrogen atom bears a cationic charge, generally over a wide pH range.

The PEI can contain at least one recurring unit of the formula (IIa) and/or (IIb) in which x is an integer in the range of about 1 to about 12, y is an integer in the range of about 1 to about 6 and z is an integer in the range of about 1 to about 13.

It will be understood that "formula II" as used herein refers to PEI that comprises formulae (IIb) and (IIa) separately or in combination.

Cationic lipopolymers comprising a recurring unit of formula (I) may be prepared by reacting a diacrylate monomer of the formula (III) with a polyethyleneimine (PEI) as shown in Scheme A below:

In formula (III), R and L have the same meanings as described above for cationic lipopolymers comprising a recurring unit of formula (I). Scheme A illustrates the preparation of a polymer comprising a recurring unit of the formula (I).

The reaction illustrated in Scheme A may be carried out by intermixing the PEI and the diacrylate (III) in a mutual solvent such as ethanol with stirring, preferably at room temperature for several hours, then evaporating the solvent to recover the resulting polymer. This invention is not bound by theory, but it is believed that the reaction between the PEI and diacrylate (III) involves a Michael reaction between one or more amines of the PEI with double bond(s) of the diacrylate. See J. March, Advanced Organic Chemistry $3^{rd}$ Ed., pp. 711-712 (1985). The diacrylate shown in Scheme A may be prepared in the manner illustrated in the Examples described below.

A wide variety of polymers comprising a recurring unit of the formula (I) may be made in accordance with Scheme A by varying the molecular weight and structure of the PEI, the size and type of the R and L groups on the diacrylate (III), and the ratio of diacrylate (III) to PEI. Mixtures of different diacrylates and/or mixtures different PEI's may be used. The PEI may be multifunctional, and thus may be capable of reacting with two or more diacrylates. Crosslinking agents may be used to produce a crosslinked cationic lipopolymer and/or the relative proportions of multifunctional PEI and diacrylate (III) may be adjusted to produce a crosslinked cationic lipopolymer. The molecular weight of the PEI is preferably less than 600 Daltons. The molar ratio of PEI to diacrylate is preferably in the range of about 1:0.5 to about 1:20. The weight average molecular weight of the cationic lipopolymer may be in the range of about 500 Daltons to about 1,000,000 Daltons, preferably in the range of about 1,000 Daltons to about 200,000 Daltons. Molecular weights may be determined by size exclusion chromatography using PEG standards or by agarose gel electrophoresis. In an embodiment, a polymer library is provided by preparing a plurality of cationic lipopolymers in which R, L, PET, and/or m are different for at least two of the polymers.

The cationic lipopolymer is preferably degradable, more preferably biodegradable, e.g., degradable by a mechanism selected from the group consisting of hydrolysis, enzyme cleavage, reduction, photo-cleavage, and sonication. This invention is not limited by theory, but it is believed that degradation of the cationic lipopolymer of formula (I) within the cell proceeds by enzymatic cleavage and/or hydrolysis of the ester linkages.

The cationic lipopolymers may form complexes with an oligonucleotide and thus are useful as carriers for the delivery of an oligonucleotide to a cell. For example, the polymer can be used to treat a mammal in need of gene therapy by administering to the mammal the polymer complexed to an oligonucleotide such as siRNA that is effective to lower or silence expression of the gene of interest. Cationic lipopolymers that comprise an oligonucleotide that is complexed to the polymer may be formed by intermixing the cationic lipopolymers and oligonucleotides in a mutual solvent, more preferably by the methods described in the examples below.

Cationic lipopolymers that comprise an oligonucleotide that is coupled to the polymer may further comprise a delivery enhancing agent capable of entering a eukaryotic cell. The delivery enhancing agent may be dissolved or mixed with the complex, or may be coupled (e.g., covalently bonded or complexed) to the cationic lipopolymer. Delivery enhancers are substances that facilitate transport of an oligonucleotide into a cell, typically by enhancing transport of an oligonucleotide/carrier complex across a membrane, reducing degradation during transport, and/or facilitating release of the oligonucleotide from the carrier. Transport of an oligonucleotide, such as a siRNA, into a cell preferably involves releasing the oligonucleotide from the carrier after the oligonucleotide/carrier complex has crossed the cell membrane, endosome membrane, and nuclear membrane. For example, in the case of siRNA, the siRNA/carrier complex first passes through the cell membrane. When this is accomplished by endocytosis, the siRNA/carrier complex is then internalized. The carrier along with the siRNA-cargo is enveloped by the cell membrane by the formation of a pocket and the pocket is subsequently pinched off. The result is a cell endosome, which is a large membrane-bound structure enclosing the siRNA cargo and the carrier. The siRNA-carrier complex then escapes through the endosome membrane into the cytoplasm, avoiding enzyme degradation in the cytoplasm, and crosses the nuclear membrane. Once in the nucleus, the siRNA cargo separates from the carrier.

In general, delivery enhancers fall into two categories: viral carrier systems and non-viral carrier systems. Because human viruses have evolved ways to overcome the barriers to transport into the nucleus discussed above, viruses or viral components are useful for transporting nucleic acids into cells. One example of a viral component useful as a delivery enhancer is the hemagglutinin peptide (HA-peptide). This viral peptide facilitates transfer of biomolecules into cells by endosome disruption. At the acidic pH of the endosome, this protein causes release of the biomolecule and carrier into the cytosol. Other examples of viral components useful as delivery enhancers are known to those skilled in the art.

Non-viral delivery enhancers are typically either polymer-based or lipid-based. They are generally polycations which act to balance the negative charge of the nucleic acid. Polycationic polymers have shown significant promise as non-viral gene delivery enhancers due in part to their ability to condense DNA plasmids of unlimited size and to safety concerns with viral vectors. Examples include peptides with regions rich in basic amino acids such as oligo-lysine, oligo-arginine or a combination thereof and PEI. These polycationic polymers are believed to facilitate transport by condensation of DNA. Branched chain versions of polycations such as PEI and starburst dendrimers can mediate both DNA condensation and endosome release. See Boussif, et al. (1995) Proc. Natl. Acad. Sci. USA vol. 92: 7297-7301. PEI can be prepared as a highly branched polymer with terminal amines that are ionizable at pH 6.9 and internal amines that are ionizable at pH 3.9. Because of this organization, PEI can generate a change in vesicle pH that leads to vesicle swelling and, eventually, release from endosome entrapment.

Another way of enhancing delivery is for the cationic lipopolymer to comprise a ligand that is recognized by a receptor on the cell that has been targeted for oligonucleotide cargo delivery. Oligonucleotide delivery into the cell may then be initiated by receptor recognition. In this context, the term "ligand" refers to a biomolecule which can bind to a specific receptor protein located on the surface of the target cell or in its nucleus or cytosol. In an embodiment, the ligand may be an antibody, hormone, pheromone, or neurotransmitter, or any biomolecule capable of acting like a ligand, which binds to the receptor. In a preferred embodiment, the ligand is an oligonucleotide. An antibody refers to any protein produced by a B lymphocyte in response to an antigen. When the ligand binds to a particular cell receptor, endocytosis is stimulated. Examples of ligands which have been used with various cell types to enhance oligonucleotide transport are galactose, transferrin, the glycoprotein asialoorosomucoid, adenovirus fiber, malaria circumsporozite protein, epidermal growth factor, human papilloma virus capsid, fibroblast growth factor and folic acid. In the case of the folate receptor, the bound ligand is internalized through a process termed potocytosis, where the receptor binds the ligand, the surrounding membrane closes off from the cell surface, and the internalized material then passes through the vesicular membrane into the cytoplasm. See Gottschalk, et al. (1994) Gene Ther 1:185-191. In one embodiment, the polymer of formula (I) and a ligand that recognizes a specific receptor of a eukaryotic cell can be used as a medical diagnostic system.

Various delivery enhancing agents are believed to function by endosome disruption. For example, in addition to the HA-protein described above, defective-virus particles have also been used as endosomolytic agents. See Cotten, et al. (July 1992) Proc. Natl. Acad. Sci. USA vol. 89: pages 6094-6098. Non-viral agents are typically either amphiphillic or lipid-based.

The release of oligonucleotides such as siRNA into the cytoplasm of the cell may be enhanced by agents that mediate endosome disruption, decrease degradation, or bypass this process all together. Chloroquine, which raises the endosomal pH, has been used to decrease the degradation of endocytosed material by inhibiting lysosomal hydrolytic enzymes. See Wagner, et al. (1990) Proc Natl Acad Sci USA vol. 87: 3410-3414. Branched chain polycations such as PEI and starburst dendrimers also promote endosome release as discussed above.

Endosomal degradation may be bypassed by incorporating subunits of toxins such as Diptheria toxin and Pseudomonas exotoxin as components of chimeric proteins that may be incorporated into the cationic lipopolymer/biomolecule complex. See Uherek, et al. (1998) J Biol. Chem. vol. 273: 8835-8841. These components promote shuttling of the nucleic acid through the endosomal membrane and back through the endoplasmic reticulum.

Once in the cytoplasm, transport of the oligonucleotide cargo to the nucleus may be enhanced by inclusion of a nuclear localization signal on the oligonucleotide carrier. For example, a specific amino acid sequence that functions as a nuclear-localization signal (NLS) may be used. It is believed that the NLS on an oligonucleotide/carrier complex interacts with a specific nuclear transport receptor protein located in the cytosol. Once the oligonucleotide/carrier complex is assembled, the receptor protein in the complex is thought to make multiple contacts with nucleoporins, thereby transporting the complex through a nuclear pore. After the oligonucleotide/carrier complex reaches its destination, it dissociates, freeing the cargo and other components. The sequence Pro-Lys-Lys-Lys-Arg-Lys-Val (SEQ ID NO.: 1) from the SV40 large T-antigen may be used for transport into nuclei. It is believed that this short sequence from SV40 large T-antigen may provide a signal that causes the transport of associated macromolecules into the nucleus.

The cationic lipopolymer may further comprise a diagnostic imaging compound such as a fluorescent, radioactive, or radio-opaque dye that is complexed to the polymer. The complex may be formed by intermixing the cationic lipopolymer and the diagnostic imaging compound in a mutual solvent. The polymer (complexed with the diagnostic imaging compound) can then be administered to a mammal and tracked using well known techniques such as PET, MRI, CT, SPECT, etc. (see Molecular Imaging of Gene Expression and Protein Function In Vivo With PET and SPECT, Vijay Sharma, PhD, Gary D. Luker, MD, and David Piwnica-Worms, MD, Ph.D., JOURNAL OF MAGNETIC RESONANCE IMAGING 16:336-351 (2002)). A diagnostic imaging composition can also be formed by combining the polymer of formula (I) with an imaging contrast agent (e.g., 1,4,7,10-Tetraazacyclododecane-1,4,7,10-tetraacetic acid (DOTA)-Gd(III) and diethylenetriaminepentaacetic acid (DTPA)-Gd(III)). If desired, the diagnostic imaging composition can further comprise a targeting agent. Suitable targeting agents include, but are not limited to, RGD peptide and galactose groups.

Another embodiment provides a pharmaceutical composition comprising: a sensitizer agent and a polymer, where the polymer comprises a recurring unit of formula (I) and an oligonucleotide, and may further comprise a delivery enhancing agent capable of entering a eukaryotic cell and/or a diagnostic imaging compound that is complexed to the polymer. The sensitizer agent may be a compound that undergoes a change in properties on exposure to light (e.g., visible and/or ultraviolet radiation) or other stimuli, thereby facilitating delivery of the biomolecule (e.g., by increasing the degradation rate of the polymer). The sensitizer agent may itself be a biomolecule that undergoes a change in activity upon stimulus. The sensitizer agent may be a light activated drug. Suitable light activated drugs include, but are not limited to, fluorescein, merocyanin, xanthene and its derivatives and the photoreactive pyrrole-derived macrocycles and their derivatives. Suitable photoreactive pyrrole-derived macrocycles include, but are not limited to, naturally occurring or synthetic porphyrins, naturally occurring or synthetic chlorins, naturally occurring or synthetic bacteriochlorins, synthetic isobateriochlorins, phthalocyanines, naphtalocyanines, and expanded pyrrole-based macrocyclic systems such as porphycenes, sapphyrins, and texaphyrins.

EXAMPLES

Example 1

Oxalyl chloride (13.5 mL, 152 mmol) was added to a solution of oleic acid 1 (10.7 g, 38 mmol) in dichloromethane (DCM, 200 mL) and N,N-dimethylformamide (DMF, three drops) at 0° C. The reaction mixture was stirred for about 1 hour and then allowed to warm to room temperature. After 1 hour, the solution was diluted with toluene and distilled. The residue was dissolved in dichloromethane (200 mL) and cooled to 0° C. Diethanolamine (10.9 mL, 114 mmol), 4-(dimethylamino)pyridine (490 mg, 4 mmol), and triethylamine (21 mL, 152 mmol) were added to the solution. The solution was stirred at 0° C. for 30 minutes and then allowed to proceed at room temperature overnight. The reaction mixture was diluted with dichloromethane and washed with 1N HCl and aqueous NaHCO₃. The organic phase was dried (Na₂SO₄) and concentrated under reduced pressure. The crude residue was then purified on a silica gel column (10:1 ethyl acetate:methanol), yielding 13.5 g (99.9%) of compound 2 as a colorless oil.

Example 2

-continued

3

Triethylamine (8.1 g, 80 mmol), DMAP (0.5 g, 4 mmol) and 2 (7.1 g, 20 mmol) was dissolved in 200 mL of dichloromethane at room temperature. The system was flushed with argon and the solution was cooled in an ice bath. Acryloyl chloride (5.4 g, 60 mmol) in 25 mL of dichloromethane was added dropwise. After the addition the reaction was allowed to warm to room temperature and stir overnight. The reaction mixture was diluted with dichloromethane and washed with water and aqueous NaHCO$_3$. The organic phase was dried (Na$_2$SO$_4$) and concentrated under reduced pressure. The crude residue was then purified on a silica gel column (1:3 ethyl acetate:hexane), yielding 7.5 g (81%) of compound 3 (molecular weight: 463.65) as a colorless oil.

Example 3

The synthesis of a cationic lipopolymer was carried out in accordance with Scheme A by reacting pentaethylenehexamine (PEHA) having a molecular weight of 232 Daltons with compound 3 as follows: About 0.1 mmol (23 mg) of PEHA (Sigma-Aldrich) and about 0.2 mmol (93 mg) of compound 3 were weighed and placed in a small vial, and 1 mL of ethanol was added and dissolved quickly. The reaction mixture was stirred for 3 hours at room temperature. Then, the reaction mixture is neutralized by adding 5 mL of 2M HCl in ether. The white precipitate YT-10 was collected by centrifugation, washed with ether for two times, and dried at room temperature under reduced pressure.

This is a general procedure that serves as a model for other synthetic procedures involving similar compounds, and may be used to synthesize a series of degradable cationic lipopolymers. The polymer YT-11 was prepared in a similar manner, except that about 0.3 mmol (139 mg) of compound 3 was used for reaction. Also, other types of PEIs were used for lipopolymer synthesis in a similar manner for YT-10 or YT-11. All the lipopolymers synthesized in Example 3 are listed in Table 1. YT-26 became a hard gel after polymerization and was not neutralized.

TABLE 1

| Name of Lipopolymer | Type of PEI | Molecular weight of PEI | Amount of PEI | Amount of compound 3 |
|---|---|---|---|---|
| YT-26 | Polyethyleneimine 600 (PEI600), | 600 | 0.1 mmol (60 mg) | 0.8 mmol (371 mg) |
| YT-10 | Pentaethylenehexamine (PEHA) | 232 | 0.1 mmol (23 mg) | 0.2 mmol (93 mg) |
| YT-11 | Pentaethylenehexamine (PEHA) | 232 | 0.1 mmol (23 mg) | 0.3 mmol (139 mg) |
| YT-22 | Tetraethylenepentamine (TEPA) | 189 | 0.1 mmol (18.9 mg) | 0.2 mmol (93 mg) |
| YT-23 | Triethylenetetramine (TETA) | 146 | 0.1 mmol (14.6 mg) | 0.2 mmol (93 mg) |
| YT-24 | Diethylenetriamine (DETA) | 103 | 0.1 mmol (10.3 mg) | 0.1 mmol (46 mg) |
| YT-25 | Ethylenediamine (EDA) | 60 | 0.1 mmol (6.0 mg) | 0.1 mmol (46 mg) |

Example 4

EGFP stable cell line: HT-1080-EGFP and HeLa-EGFP stable cell lines were originated from HT-1080 and HeLa cells respectively with stable enhanced green fluorescence protein (EGFP) gene expression, prepared by transfecting pEGFP-N1 plasmid DNA (BD Biosciences Clontech) to HT-1080 and HeLa cells. Transfected cells were selected and cloned by using neomycin resistance capability, carried on pEGFP-N1 plasmid. Cell culture was maintained in Dulbecco's Modified Eagle's Medium (DMEM) containing 10% Bovine serum, 100 units/ml penicillin and 100 µg/ml streptomycin at 37° C., 5% $CO_2$. EGFP expression can be observed under fluorescence microscope (Olympus). Both HT-1080-EGFP and HeLa-EGFP cells showed bright green fluorescence by the combination of blue excitation light and green emission filter setting.

Example 5 siRNA delivery study: The siRNA targeting EGFP gene was synthesized by Dharmacon Research Inc. siRNA targeting EGFP and luciferase gene were 21 bp double strand RNA, the sequence of sense strand of them were NNC GAG AAG CGC GAU CAC AUG (SEQ ID NO.: 2).

$1.5 \times 10^4$ HT-1080-EGFP and HeLa-EGFP cells were planted in 96-well plate for each well at 24 h before transfection. For each well, an aliquot of 7.5 µL of solution containing 1.5 µg of lipopolymer was added into 7.5 µL DNA solution containing 15 pmol siRNA and mixed completely. The DNA and lipopolymer mixture were incubated for 15 minutes at room temperature to allow for the formation of siRNA-lipopolymer complexes. The complexes were added to each well and the cells were incubated at 37° C., 5% $CO_2$ for 48 hrs. Lipofectamine were used as positive controls. The siRNA delivery efficiency was determined by GFP signal analysis.

Figure 1:
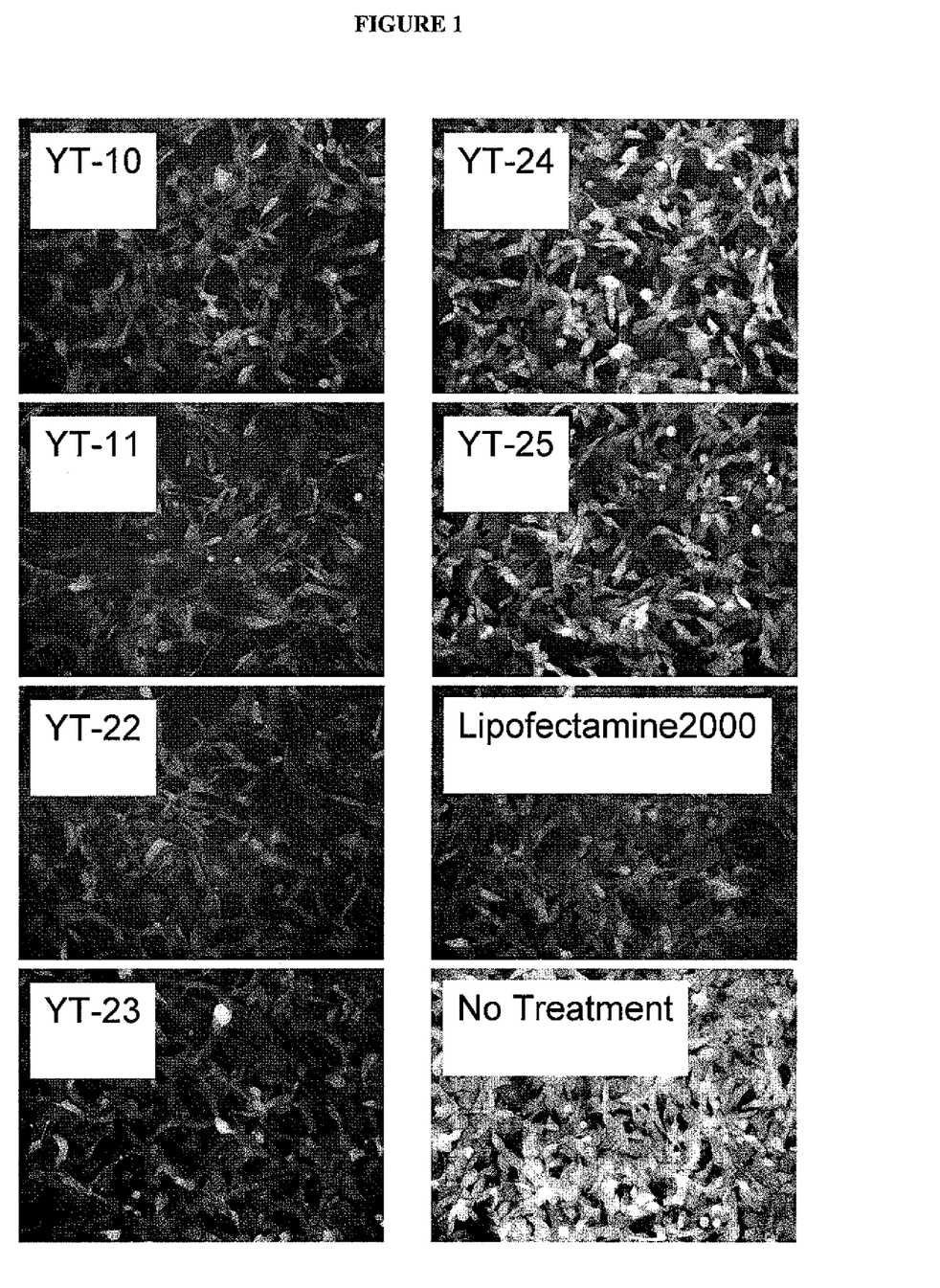
FIG. 1 is a photograph of enhanced green fluorescence proteins (EGFP) expression in HT-1080-EGFP cells after treatment with siRNA complexed to the lipopolymers (YT-10, YT-11, YT-22, YT-23, YT-24 and YT-25), lipofectamine 2000 (positive control), and without any treatment (negative control).

FIG. 1 is a photograph of enhanced green fluorescence proteins (EGFP) expression in HT-1080-EGFP cells after treatment of siRNA with lipopolymers (YT-10, YT-11, YT-22, YT-23, YT-24 and YT-25), lipofectamine 2000 (positive control), and without any treatment (negative control).

Figure 2:
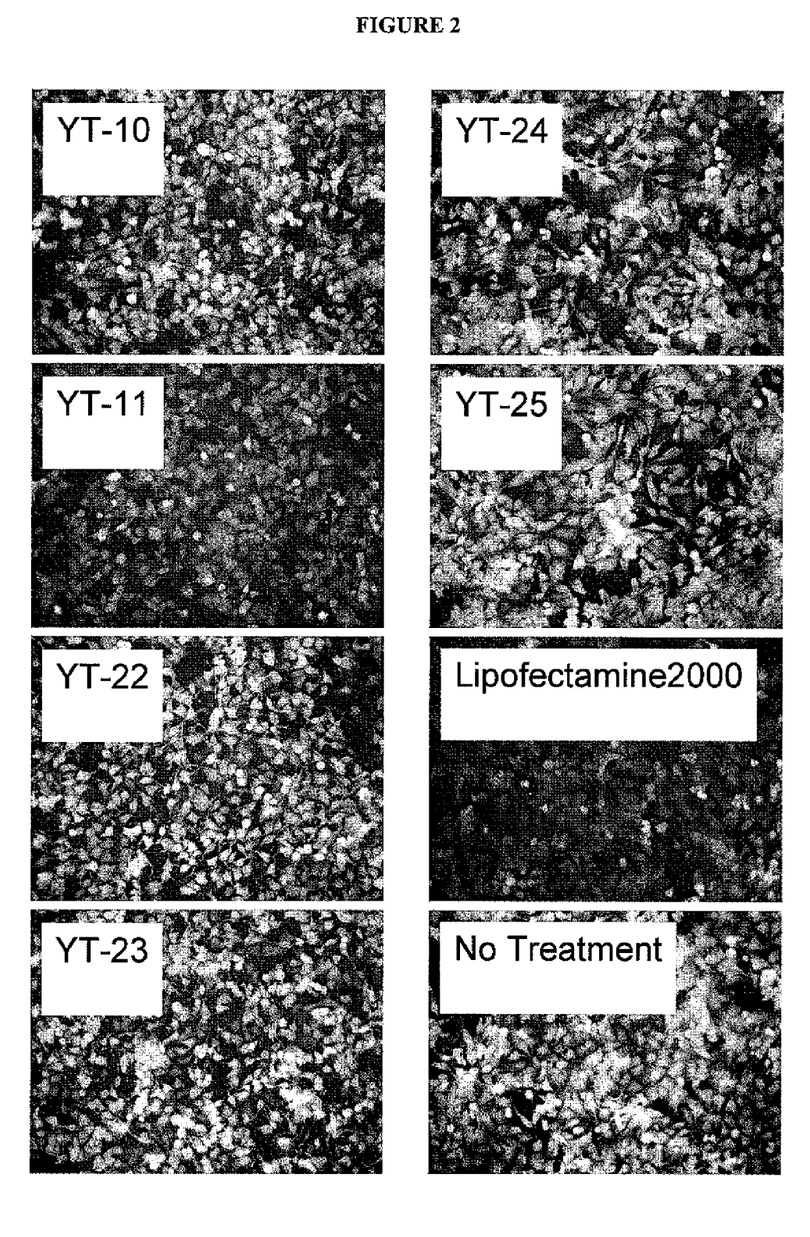
FIG. 2 is a photograph of enhanced green fluorescence proteins (EGFP) expression in HeLa-EGEP cells after treatment with siRNA complexed to the lipopolymers (YT-10, YT-11, YT-22, YT-23, YT-24 and YT-25), lipofectamine 2000 (positive control), and without any treatment (negative control).

FIG. 2 is a photograph of enhanced green fluorescence proteins (EGFP) expression in HeLa-EGFP cells after treatment of siRNA with lipopolymers (YT-10, YT-11, YT-22, YT-23, YT-24 and YT-25), lipofectamine 2000 (positive control), and without any treatment (negative control).

As shown in FIGS. 1 and 2, without any treatment of silenced targeting siRNA, EGFP expression was not inhibited, as indicated by the strong fluorescence. See No Treatment of FIGS. 1 and 2. With treatment of silenced targeting siRNA with the lipopolymers carriers, EGFP expression was inhibited, as indicated by the weak fluorescence. See YT-10, YT-11, YT-22, YT-23, YT-24, YT-25, and Lipofectamine2000 of FIGS. 1 and 2. In HT-1080-EGFP cells, YT-10, YT-11, YT-22 and YT-23 showed significant inhibiting effect on EGFP expression. YT-24 and YT-25 also showed effective siRNA delivery. Additionally, YT-11 showed an ability to deliver siRNA. These results indicate that the lipopolymers are better or comparable delivery agents of siRNA compared to commercial Lipofectamine2000.

Although the invention has been described with reference to embodiments and examples, it should be appreciated by those skilled in the art that various omissions, additions and modifications may be made to the compositions and methods described above without departing from the scope of the invention, and all such modifications and changes are intended to fall within the scope of the invention. Accordingly, the invention is only limited by the following claims.

---

What is claimed is:

1. A polymer comprising a recurring unit selected from the group consisting of formula (I):

wherein:
PEI is a polyethyleneimine recurring unit having a molecular weight less than 600 Daltons;
R is selected from the group consisting of an electron pair, hydrogen, $C_2$-$C_{10}$ alkyl, $C_2$-$C_{10}$ heteroalkyl, $C_5$-$C_{30}$ aryl, and $C_2$-$C_{30}$ heteroaryl;
L is selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl, $C_2$-$C_{50}$ heteroaryl, $C_2$-$C_{50}$ alkynyl, $C_2$-$C_{50}$ heteroalkynyl, $C_2$-$C_{50}$ carboxyalkenyl and $C_2$-$C_{50}$ carboxyheteroalkenyl; and
m is an integer in the range of about 1 to about 30.

2. The polymer of claim 1 in which the PEI comprises at least one recurring unit selected from the group consisting of formula (IIa) and formula (IIb):

wherein x is an integer in the range of about 1 to about 12, y is an integer in the range of about 1 to about 6, and z is an integer in the range of about 1 to about 13.

3. The polymer of claim 1 that is biodegradable.

4. The polymer of claim 1 that is degradable by a mechanism selected from the group consisting of hydrolysis, enzyme cleavage, reduction, photo-cleavage, and sonication.

5. The polymer of claim 1 in which L is selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_2$-$C_{50}$ alkynyl and $C_2$-$C_{50}$ heteroalkynyl.

6. The polymer of claim 1 in which L is selected from the group consisting of $C_{12}$ to $C_{18}$ fatty acid, cholesterol, $C_{12}$ to $C_{18}$ fatty acid derivative, and cholesterol derivative.

7. The polymer of claim 1 having a weight average molecular weight in the range of about 500 Daltons to about 1,000,000 Daltons.

8. The polymer of claim 1 having a weight average molecular weight in the range of about 1,000 Daltons to about 200,000 Daltons.

9. The polymer of claim 1 which is crosslinked.

10. A composition comprising an oligonucleotide that is complexed to the polymer of claim 1.

11. The composition of claim 10 in which the oligonucleotide is selected from the group consisting of a RNA-oligomer and a DNA-oligomer.

12. The composition of claim 10 in which the oligonucleotide is siRNA or antisense.

13. The composition of claim 10 further comprising a delivery enhancing agent capable of entering a eukaryotic cell.

14. The composition of claim 13 further comprising a diagnostic imaging compound that is complexed to the polymer.

15. The composition of claim 13 in which the delivery enhancing agent facilitates one or more functions in the eukaryotic cell selected from the group consisting of receptor recognition, internalization, escape of the oligonucleotide from cell endosome, nucleus localization, and oligonucleotide release.

16. The composition of claim 15 in which the oligonucleotide is selected from the group consisting of siRNA and antisense.

17. The composition of claim 13 in which the delivery enhancing agent is coupled to the polymer.

18. A polymer comprising a recurring unit selected from the group consisting of formula (I):

wherein:
PEI is a polyethyleneimine recurring unit comprising at least one recurring unit of the formula (IIb):

wherein z is an integer in the range of about 1 to about 13;
R is selected from the group consisting of an electron pair, hydrogen, $C_2$-$C_{10}$ alkyl, $C_2$-$C_{10}$ heteroalkyl, $C_5$-$C_{30}$ aryl, and $C_2$-$C_{30}$ heteroaryl;
L is selected from the group consisting of $C_2$-$C_{50}$ alkyl, $C_2$-$C_{50}$ heteroalkyl, $C_2$-$C_{50}$ alkenyl, $C_2$-$C_{50}$ heteroalkenyl, $C_5$-$C_{50}$ aryl, $C_2$-$C_{50}$ heteroaryl, $C_2$-$C_{50}$ alkynyl, $C_2$-$C_{50}$ heteroalkynyl, $C_2$-$C_{50}$ carboxyalkenyl and $C_2$-$C_{50}$ carboxyheteroalkenyl; and
m is an integer in the range of about 1 to about 30.

19. The polymer of claim 18, wherein the PEI has a molecular weight of less than 600 Daltons.

20. The polymer of claim 18, wherein the PEI further comprises a recurring unit of the formula IIa:

wherein x is an integer in the range of about 1 to about 12 and y is an integer in the range of about 1 to about 6.

21. The polymer of claim 20, wherein the PEI has a molecular weight of less than 600 Daltons.

22. A method of transfecting a eukaryotic cell, comprising contacting the cell with the composition of claim 11 to thereby deliver the oligonucleotide to the cell.

23. A polymer library comprising a plurality of polymers of claim 1, wherein at least one parameter selected from the group consisting of R, L, PEI and m is different for at least two of the polymers.

* * * * *